United States Patent
Joo et al.

(10) Patent No.: US 10,033,007 B2
(45) Date of Patent: Jul. 24, 2018

(54) ORGANIC LIGHT EMITTING DIODE

(71) Applicant: LG DISPLAY CO., LTD., Seoul (KR)

(72) Inventors: Mun Kyu Joo, Daejeon (KR); Minsoo Kang, Daejeon (KR); Jeamin Moon, Daejeon (KR); Jina You, Daejeon (KR)

(73) Assignee: LG DISPLAY CO., LTD., Seoul (KR)

( * ) Notice: Subject to any disclaimer, the term of this patent is extended or adjusted under 35 U.S.C. 154(b) by 269 days.

(21) Appl. No.: 14/768,122

(22) PCT Filed: Jun. 7, 2013

(86) PCT No.: PCT/KR2013/005053
§ 371 (c)(1),
(2) Date: Aug. 14, 2015

(87) PCT Pub. No.: WO2014/196677
PCT Pub. Date: Dec. 11, 2014

(65) Prior Publication Data
US 2016/0020421 A1 Jan. 21, 2016

(51) Int. Cl.
*H01L 51/50* (2006.01)
*H01L 27/32* (2006.01)
(Continued)

(52) U.S. Cl.
CPC .......... *H01L 51/504* (2013.01); *C07D 311/82* (2013.01); *C07D 487/14* (2013.01);
(Continued)

(58) Field of Classification Search
None
See application file for complete search history.

(56) References Cited

U.S. PATENT DOCUMENTS 4,780,536 A   10/1988  Czarnik et al.
5,645,948 A    7/1997  Shi et al.
(Continued)

FOREIGN PATENT DOCUMENTS

CN   1602128 A   3/2005
CN   1742518 A   3/2006
(Continued)

OTHER PUBLICATIONS

Lee, Jeong-Hwan, et al., "A high performance transparent inverted organic light emitting diode with 1,4,5,8,9,11-hexaazatriphenylenehexacarbonitrile as an organic buffer layer," J. Matter, Chem., 2012, vol. 22, pp. 15262-15266.

*Primary Examiner* — J. L. Yang
(74) *Attorney, Agent, or Firm* — Dentons US LLP

(57) ABSTRACT

The present invention relates to an organic light emitting device, and comprises a first cathode, a second cathode, and an anode provided between the first cathode and the second cathode, in which a first light emitting unit is provided between the first cathode and the anode, a second light emitting unit is provided between the second cathode and the anode, and the first light emitting unit and the second emitting unit are connected in parallel with each other, the first light emitting unit comprises a first light emitting layer, and an organic material layer comprising the compound represented by Formula 1 is provided between the first light emitting layer and the anode, and the second light emitting unit comprises a second light emitting layer, and an organic material layer comprising the compound represented by Formula 1 is provided between the second light emitting layer and the anode.

11 Claims, 3 Drawing Sheets

(51) Int. Cl.
*H01L 51/52* (2006.01)
*H01L 51/00* (2006.01)
*C07D 487/14* (2006.01)
*C07D 311/82* (2006.01)

(52) U.S. Cl.
CPC ...... *H01L 27/3202* (2013.01); *H01L 27/3209* (2013.01); *H01L 51/0072* (2013.01); *H01L 51/5206* (2013.01); *H01L 51/0085* (2013.01); *H01L 51/5234* (2013.01); *H01L 2251/301* (2013.01); *H01L 2251/308* (2013.01); *H01L 2251/5323* (2013.01); *H01L 2251/558* (2013.01)

(56) References Cited

U.S. PATENT DOCUMENTS

| | | | |
|---|---|---|---|
| 6,436,559 | B1 | 8/2002 | Ueno et al. |
| 6,720,573 | B2 * | 4/2004 | Son .................... C07D 487/14 257/40 |
| 2002/0158242 | A1 | 10/2002 | Son et al. |
| 2003/0165715 | A1 | 9/2003 | Yoon et al. |
| 2003/0168970 | A1 | 9/2003 | Tominaga et al. |
| 2004/0036412 | A1 | 2/2004 | Takamura |
| 2005/0062408 | A1 | 3/2005 | Yoo et al. |
| 2005/0184659 | A1 | 8/2005 | Ibe |
| 2006/0145604 | A1 * | 7/2006 | Liao .................... H01L 51/5052 313/506 |
| 2006/0289882 | A1 | 12/2006 | Nishimura et al. |
| 2007/0092755 | A1 | 4/2007 | Begley et al. |
| 2007/0122656 | A1 | 5/2007 | Klubek et al. |
| 2007/0200490 | A1 | 8/2007 | Kawamura et al. |
| 2007/0267958 | A1 | 11/2007 | Kitazawa et al. |
| 2009/0009101 | A1 | 1/2009 | Kang et al. |
| 2009/0091248 | A1 | 4/2009 | Kim et al. |
| 2010/0108990 | A1 | 5/2010 | Hosokawa et al. |
| 2010/0308353 | A1 | 12/2010 | Grabowski et al. |
| 2011/0079774 | A1 | 4/2011 | Kang et al. |
| 2012/0326132 | A1 | 12/2012 | Ko et al. |
| 2013/0240847 | A1 * | 9/2013 | Zakhidov ............ H01L 27/3202 257/40 |

FOREIGN PATENT DOCUMENTS

| | | |
|---|---|---|
| CN | 1744786 A | 3/2006 |
| CN | 101371619 A | 2/2009 |
| JP | 2000-58260 A | 2/2000 |
| JP | 2007-039405 A | 2/2007 |
| JP | 2012-221902 A | 11/2012 |
| KR | 2003-0067773 A | 8/2003 |
| KR | 10-2004-0065667 A | 7/2004 |
| KR | 10-2007-0052764 A | 5/2007 |
| KR | 10-2007-0076521 A | 7/2007 |
| KR | 10-2007-0118711 A | 12/2007 |
| KR | 10-0845694 B1 | 7/2008 |
| KR | 10-2010-0126428 A | 12/2010 |
| KR | 10-2013-0006937 A | 1/2013 |
| WO | 2005-097756 A1 | 10/2005 |
| WO | 2011-146915 A1 | 11/2011 |

* cited by examiner

[Figure 1]
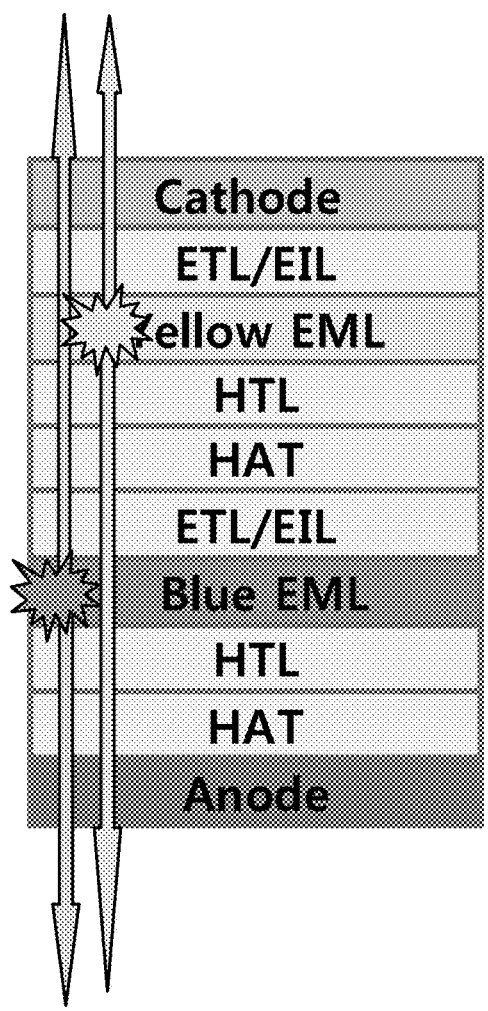

[Figure 2]
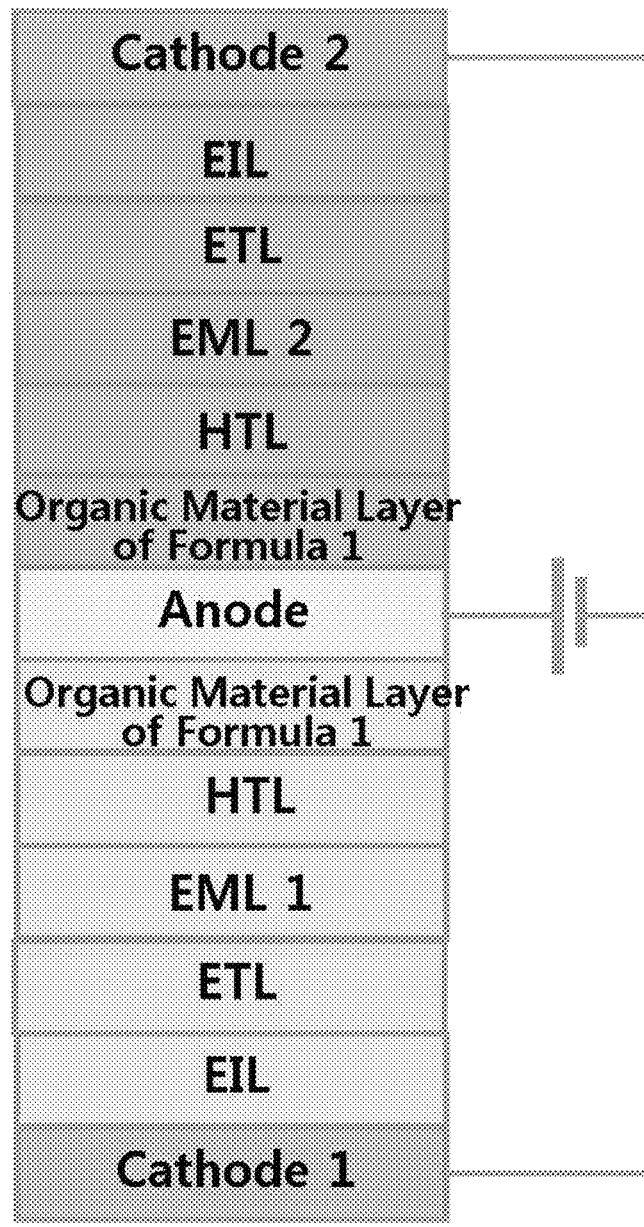

[Figure 3]
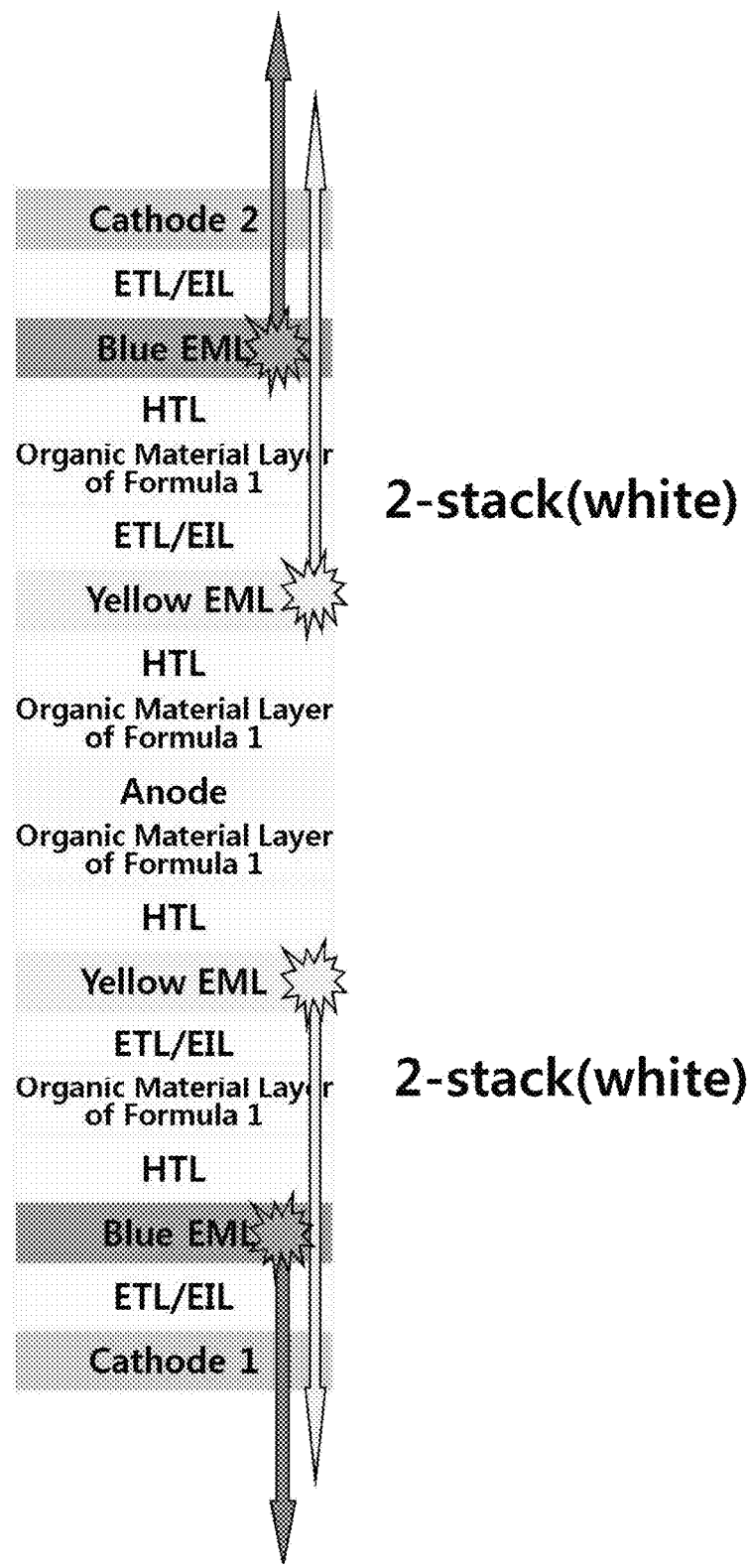

ORGANIC LIGHT EMITTING DIODE

This application is a National Stage Entry of International Application No. PCT/KR2013/005053, filed Jun. 7, 2013, which is incorporated by reference in its entirety for all purposes as if fully set forth herein.

TECHNICAL FIELD

The present invention relates to an organic light emitting device.

BACKGROUND ART

An organic light emitting device converts a current into visible light by injecting electrons and holes from two electrodes into an organic material layer. The organic light emitting device may have a multilayer structure comprising two or more organic material layers. For example, the organic light emitting device may further comprise an electron or hole injection layer, an electron or hole blocking layer, or an electron or hole transporting layer if necessary, in addition to a light emitting layer.

Recently, as the use of the organic light emitting layer has been diversified, studies on materials, which may improve the performance of the organic light emitting device, have been actively conducted.

DETAILED DESCRIPTION OF THE INVENTION

Technical Problem

The present specification describes an organic light emitting device having a novel structure.

Technical Solution

An exemplary embodiment of the present invention provides an organic light emitting device comprising a first cathode, a second cathode, and an anode provided between the first cathode and the second cathode, in which a first light emitting unit is provided between the first cathode and the anode, a second light emitting unit is provided between the second cathode and the anode, and the first light emitting unit and the second emitting unit are connected in parallel with each other, the first light emitting unit comprises a first light emitting layer, and an organic material layer comprising a compound represented by the following Formula 1 is provided between the first light emitting layer and the anode, and the second light emitting unit comprises a second light emitting layer, and an organic material layer comprising the compound represented by the following Formula 1 is provided between the second light emitting layer and the anode.

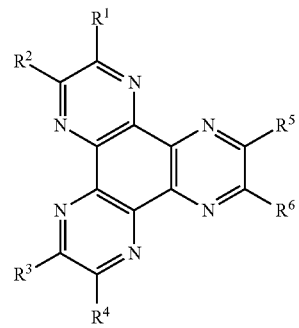

[Formula 1]

In Formula 1, $R^1$ to $R^6$ are the same as or different from each other, and each independently hydrogen, a halogen atom, nitrile (—CN), nitro (—NO$_2$), sulfonyl (—SO$_2$R), sulfoxide (—SOR), sulfonamide (—SO$_2$NR), sulfonate (—SO$_3$R), trifluoromethyl (—CF$_3$), ester (—COOR), amide (—CONHR or —CONRR'), a substituted or unsubstituted straight or branched $C_1$ to $C_{12}$ alkoxy, a substituted or unsubstituted straight or branched $C_1$ to $C_{12}$ alkyl, a substituted or unsubstituted straight or branched $C_2$ to $C_{12}$ alkenyl, a substituted or unsubstituted aromatic or non-aromatic heterocyclic ring, a substituted or unsubstituted aryl, a substituted or unsubstituted mono- or di-aryl amine, or a substituted or unsubstituted aralkyl amine, in which R and R' are each independently a substituted or unsubstituted $C_1$ to $C_{60}$ alkyl, a substituted or unsubstituted aryl, or a substituted or unsubstituted 5- to 7-membered heterocyclic ring.

Advantageous Effects

The organic light emitting device according to the present invention may be applied to a dual emission type organic light emitting device by symmetrically connecting two light emitting units to an anode, which is a common electrode, on and under the anode. Further, in the organic light emitting device according to the present invention, an electrode material having various work functions may be used by comprising organic material layers comprising the compound represented by Formula 1.

BRIEF DESCRIPTION OF DRAWINGS

FIG. 1 a view schematically illustrating a stacked structure of an organic light emitting device according to the related art.

FIG. 2 is a view schematically illustrating a stacked structure of an organic light emitting device according to an exemplary embodiment of the present invention.

FIG. 3 is a view schematically illustrating a stacked structure of an organic light emitting device according to an exemplary embodiment of the present invention.

BEST MODE

Hereinafter, embodiments exemplified in the present specification will be described in detail.

In general, an organic light emitting device in the related art has a structure in which light is emitted to only one direction. In such a structure, when an anode and a cathode are used as a transparent electrode, it is possible to achieve dual emission of the organic light emitting device, but since light is emitted from both sides, there occurs a phenomenon that brightness of the device on one side is decreased by half.

In addition, the following FIG. 1 illustrates an organic light emitting device in the related art. More specifically, the organic light emitting device in the related art may comprise an anode, a cathode, and an organic material layer comprising a light emitting layer between the anode and the cathode. In particular, the organic light emitting device in the related art may comprise two light emitting layers in the organic material layer in order to emit white color light, but since cavity lengths according to wavelengths of the light emitting layers are different from each other, the colors of lights emitted from both sides thereof may be different from each other, and accordingly, there is a problem in that it is difficult to implement a desired color.

Thus, in the present invention, a structure of an organic light emitting device for connecting two or more light emitting units in parallel in a vertical direction has been introduced, and particularly, an organic light emitting device in which an electrode structure may be further simplified by using the anode as a common electrode has been developed.

An organic light emitting device according to an exemplary embodiment of the present invention comprises a first cathode, a second cathode, and an anode provided between the first cathode and the second cathode, in which a first light emitting unit is provided between the first cathode and the anode, a second light emitting unit is provided between the second cathode and the anode, and the first light emitting unit and the second emitting unit are connected in parallel with each other, the first light emitting unit comprises a first light emitting layer, and an organic material layer comprising a compound represented by the following Formula 1 is provided between the first light emitting layer and the anode, and the second light emitting unit comprises a second light emitting layer, and an organic material layer comprising the compound represented by the following Formula 1 is provided between the second light emitting layer and the anode.

In the present invention, at least one of the organic material layers comprising the compound represented by Formula 1 may be an organic material layer which is in contact with the anode. Furthermore, both the organic material layer comprising the compound represented by Formula 1, which is provided between the first light emitting layer and the anode, and the organic material layer comprising the compound represented by Formula 1, which is provided between the second light emitting layer and the anode, may be an organic material layer which is in contact with the anode.

In the present invention, the compound of Formula 1 may be exemplified as compounds of the following Formulas 1-1 to 1-6, but is not limited thereto.

[Formula 1-1]

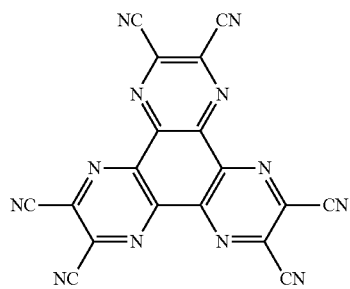

[Formula 1-2]

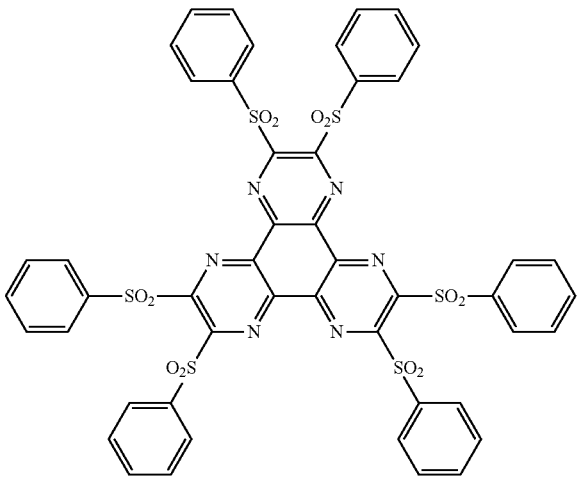

[Formula 1-3]

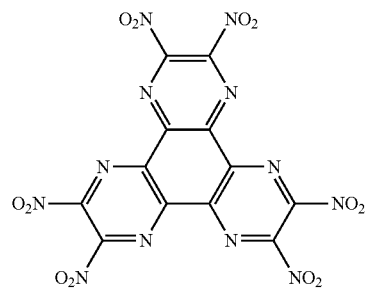

[Formula 1-4]

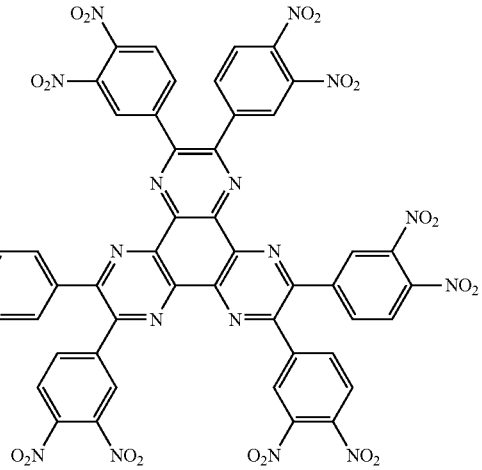

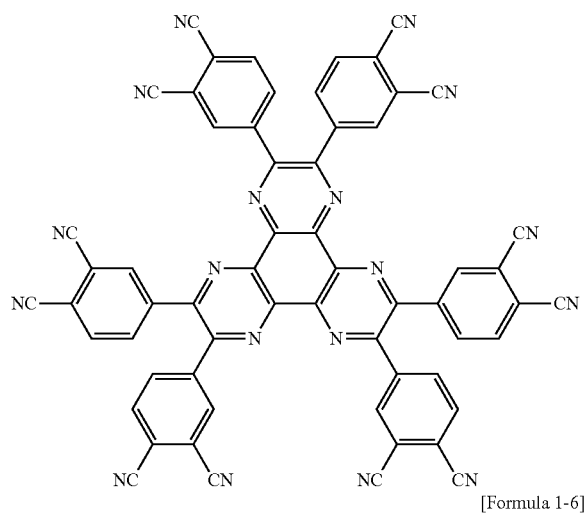
[Formula 1-5]

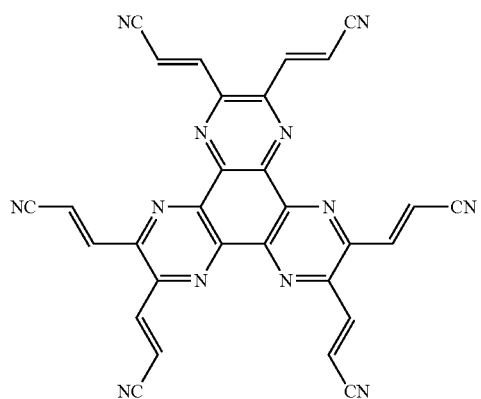
[Formula 1-6]

Other examples, or synthesis methods and various characteristics of Formula 1 are described in US Patent Application No. 2002-0158242, and U.S. Pat. Nos. 6,436,559 and 4,780,536, and the contents of these documents are all incorporated in the present specification.

Hereinafter, each layer constituting the organic light emitting device according to an exemplary embodiment of the present invention will be described in detail. Materials of each layer to be described below may be a single material or a mixture of two or more materials.

In the present specification, an n-type means n-type semiconductor characteristics. In other words, an n-type organic material layer is an organic material layer having a characteristic that electrons are injected or transported at the LUMO energy level, and an organic material layer having a characteristic of a material having electron mobility greater than hole mobility. Conversely, a p-type means p-type semiconductor characteristics. In other words, a p-type organic material layer is an organic material layer having a characteristic that holes are injected or transported at the highest occupied molecular orbital (HOMO) energy level, and an organic material layer having a characteristic of a material having hole mobility greater than electron mobility. In the present specification, "an organic material layer which transports electric charges at the HOMO energy level" and the p-type organic material layer may be used as having the same meaning. Further, "an organic material layer which transports electric charges at the LUMO energy level" and the n-type organic material layer may be used as having the same meaning.

In the present specification, an energy level means a size of energy. Therefore, even when an energy level is expressed in a negative (−) direction from the vacuum level, the energy level is interpreted to mean an absolute value of the corresponding energy value. For example, the HOMO energy level means a distance from the vacuum level to the highest occupied molecular orbital. In addition, the LUMO energy level means a distance from the vacuum level to the lowest unoccupied molecular orbital.

In the present specification, an electric charge means an electron or a hole.

Anode

An anode may comprise a metal, a metal oxide, or a conductive polymer. The conductive polymer may comprise an electrically conductive polymer. The anode may have a work function value from about 3.5 eV to about 5.5 eV. Examples of conductive materials comprise carbon, aluminum, vanadium, chromium, copper, zinc, silver, gold, other metals, and an alloy thereof; zinc oxide, indium oxide, tin oxide, indium tin oxide (ITO), indium zinc oxide, and other similar metal oxides; a mixture of oxide and metal such as ZnO:Al and SnO$_2$:Sb oxide, and the like. As a material for the anode, a transparent material or an opaque material may be used. In the case of a structure in which light is emitted in the anode direction, the anode may be transparently formed. Here, transparency is sufficient as long as light emitted from an organic material layer may be transmitted, and the transmittance of light is not particularly limited.

In particular, the organic light emitting device according to the present invention may be more usefully applied to a dual emission type organic light emitting device by comprising the anode as a common electrode.

In the present invention, a p-type organic material layer may be each provided between the first light emitting layer or the second light emitting layer and the anode. The p-type organic material layer may be a hole injection layer (HIL), or a hole transporting layer (HTL).

As a material for the p-type organic material layer, an aryl amine compound may be used. As an example of the aryl amine compound, there is a compound of the following Formula 2.

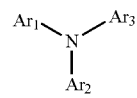
[Formula 2]

In Formula 2, $Ar_1$, $Ar_2$, and $Ar_3$ are each independently hydrogen or a hydrocarbon group, at least one of $Ar_1$, $Ar_2$, and $Ar_3$ comprises an aromatic hydrocarbon substitute, and respective substitutes may be the same as each other and may also be composed of different substitutes.

Specific examples of Formula 2 comprise the following formulas, and the range of exemplary embodiments described in the present specification is not always limited thereto.

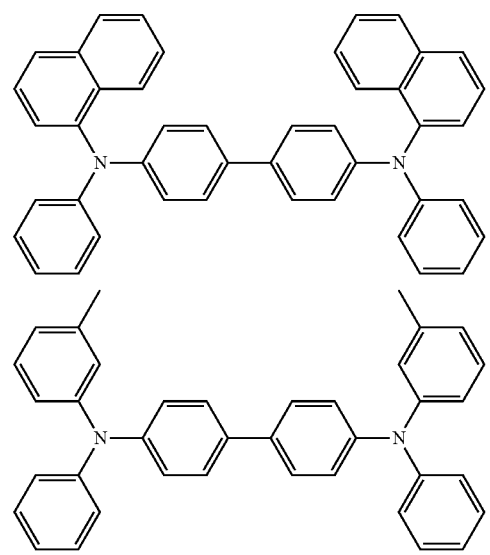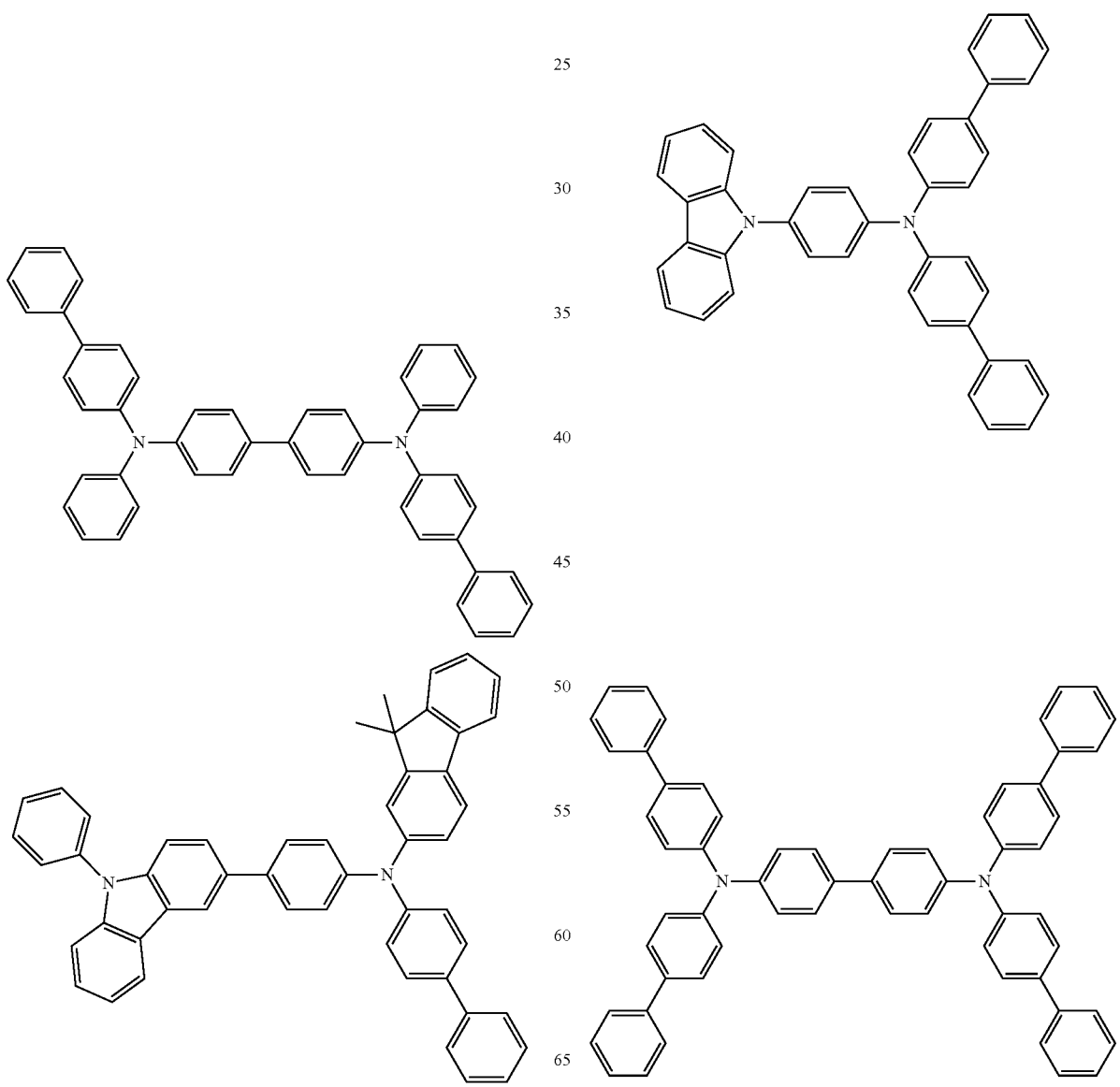

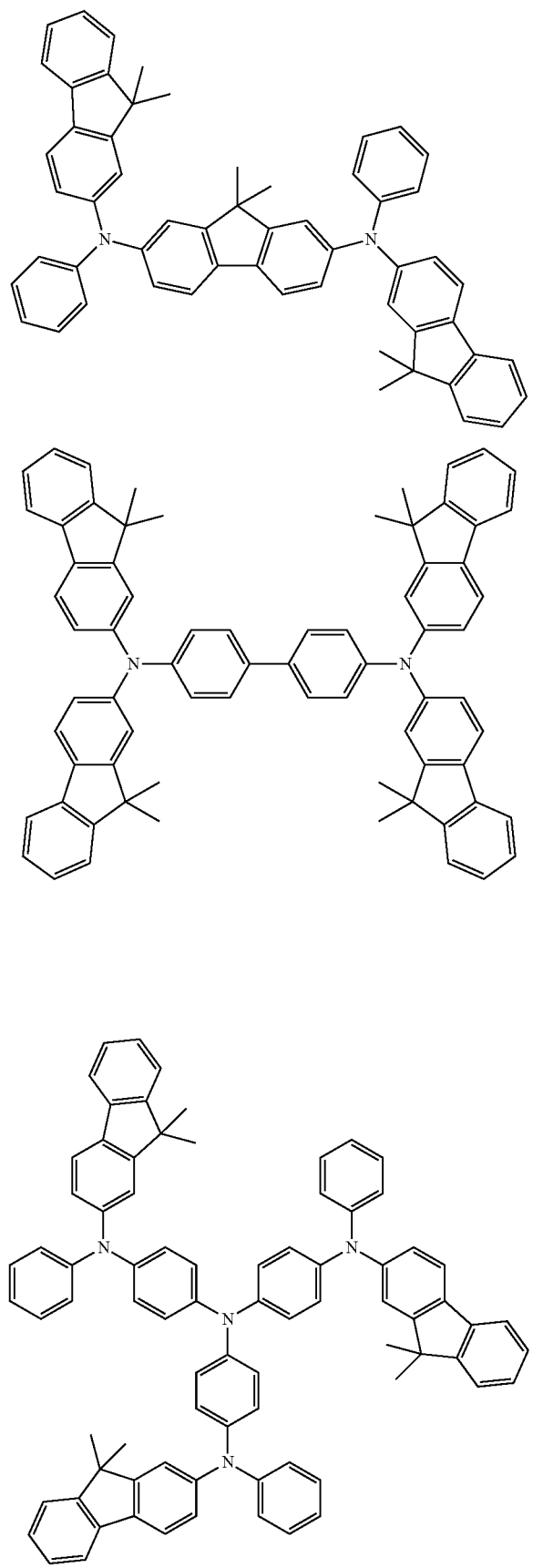
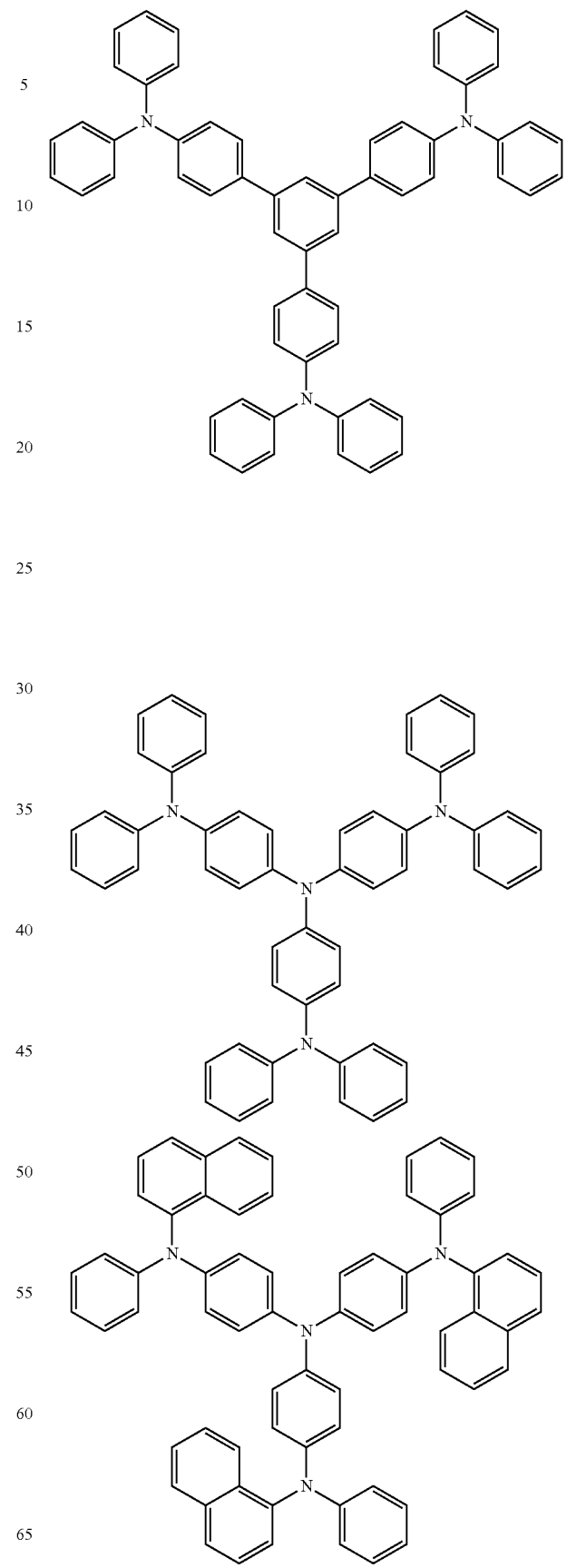

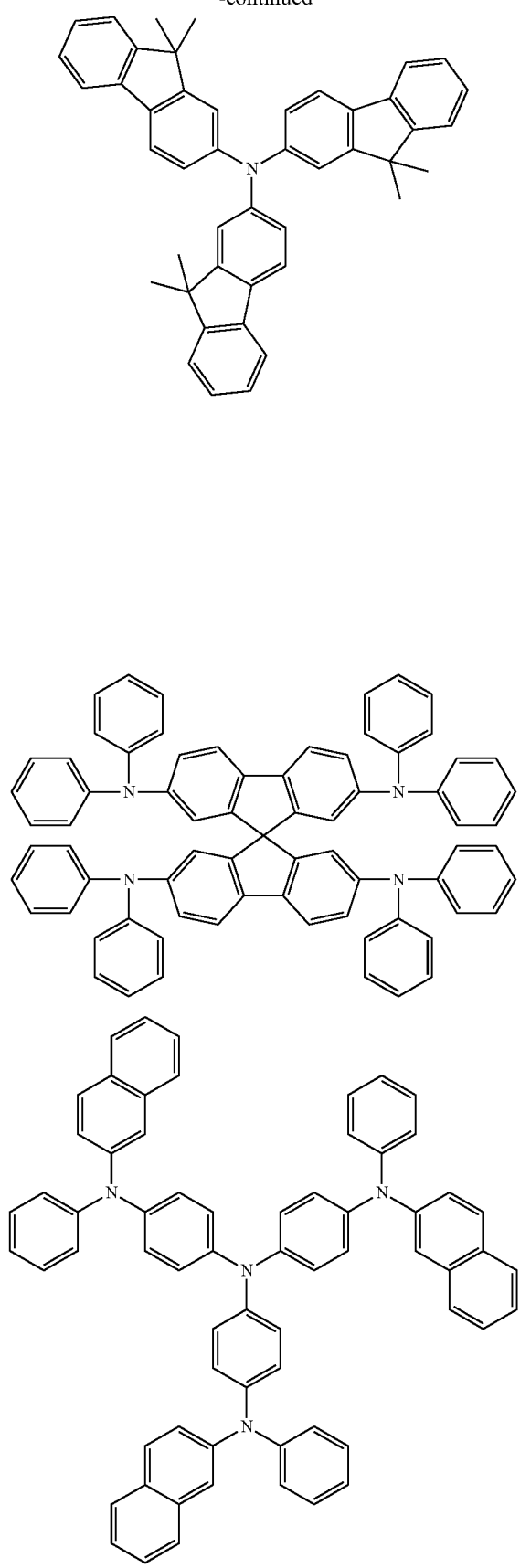
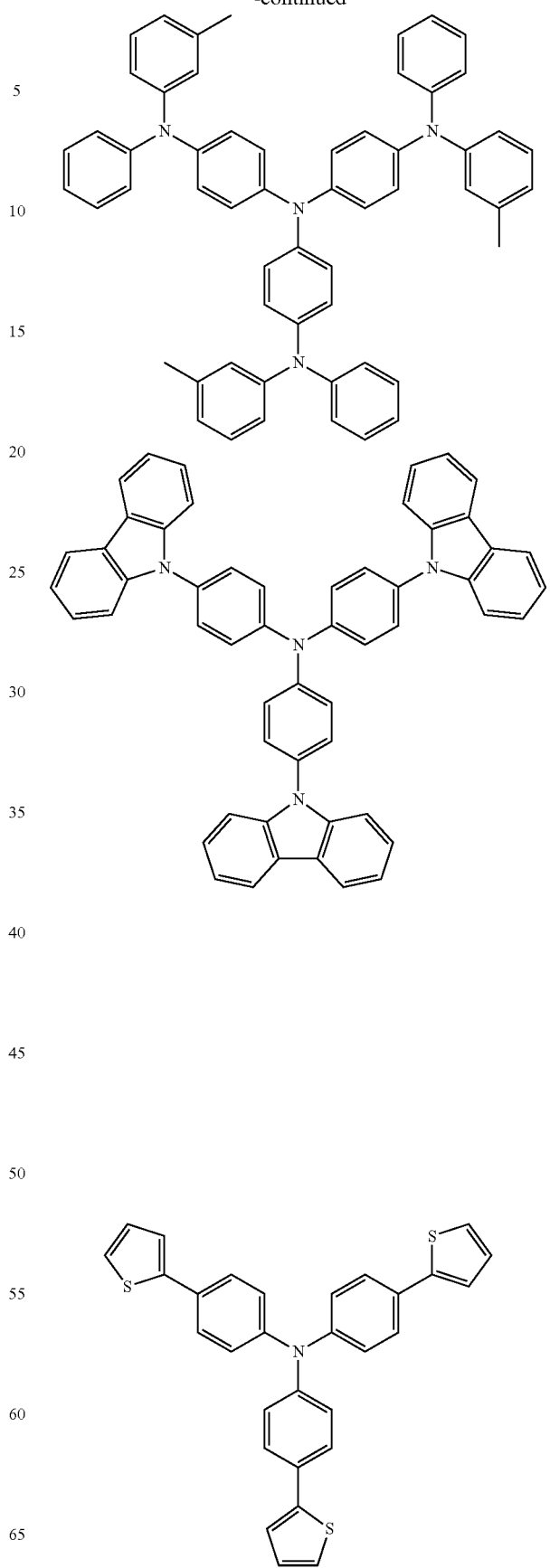

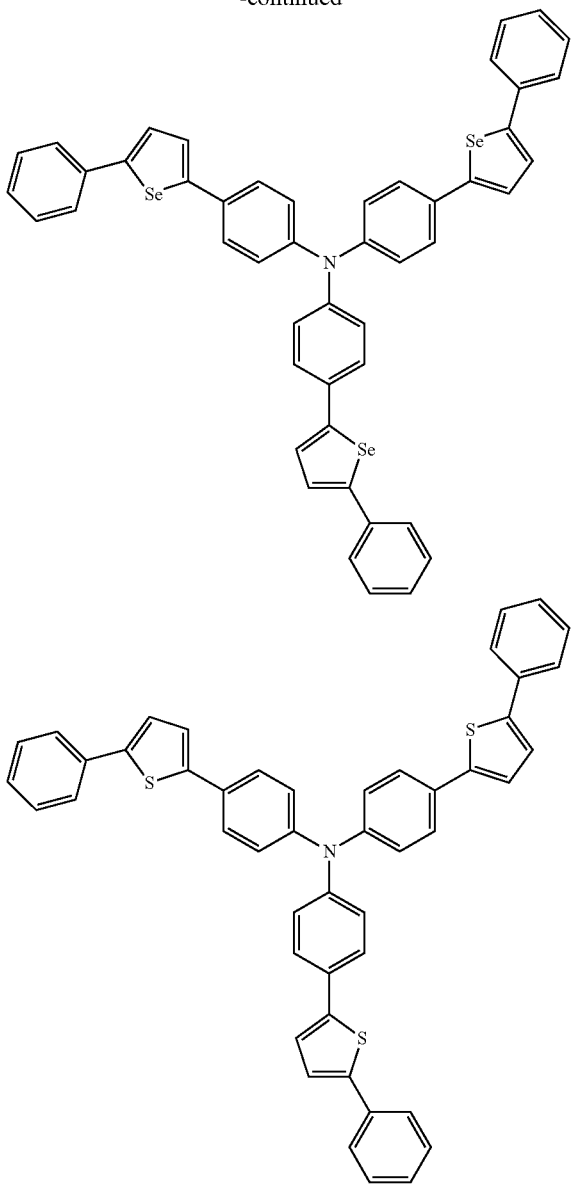

The p-type organic material layer is differentiated from a layer having p-type semiconductor characteristics by doping the organic material in the related art with a p-type dopant. The p-type organic material layer does not exhibit p-type semiconductor characteristics by the p-type dopant, but the p-type organic material layer itself comprises an organic material having p-type semiconductor characteristics.

Light Emitting Layer (EML)

Since hole transfer and electron transfer simultaneously occur in the first light emitting layer and the second light emitting layer of the present invention, the first light emitting layer and the second light emitting layer may have both n-type characteristics and p-type characteristics. For convenience, when electron transport is faster than hole transport, the light emitting layer may be defined as an n-type light emitting layer, and when hole transport is faster than electron transport, the light emitting layer may be defined as a p-type light emitting layer.

The n-type light emitting layer comprises aluminum tris (8-hydroxy quinoline) (Alq$_3$); 8-hydroxy quinoline beryllium (BAlq); a benzoxazole-based compound, a benzthiazole-based compound or benzimidazole-based compound; a polyfluorene-based compound; a sila cyclopentadiene (silole)-based compound, and the like, but is not limited thereto.

The p-type light emitting layer comprises a carbazole-based compound; an anthracene-based compound; a polyphenylenevinylene (PPV)-based polymer; or a spiro compound, and the like, but is not limited thereto.

Electron Transporting Layer (ETL) and Electron Injection Layer (EIL)

In the present invention, an n-type organic material layer may be each provided between the first light emitting layer or the second light emitting layer and the cathode. The n-type organic material layer may be an electron injection layer (EIL), or an electron transporting layer (ETL).

It is preferred that a material for the n-type organic material layer is a material having a large electron mobility so as to transport electrons well. The electron transporting layer comprises, aluminum tris(8-hydroxy quinoline) (Alq$_3$); an organic compound comprising an Alq$_3$ structure; a hydroxyflavone-metal complex or a sila cyclopentadiene (silole)-based compound, and the like, but is not limited thereto.

Moreover, as a material for the n-type organic material layer, it is possible to use a material for the n-type organic material layer used as an electron injection or transporting material, which is known in the art. Specifically, the following material may be used, but is not limited thereto. For example, as an example of the material for the n-type organic material layer, it is possible to use a compound having a functional group selected from an imidazole group, an oxazole group, a thiazole group, a quinoline group, and a phenanthroline group.

Specific examples of the compound having a functional group selected from an imidazole group, an oxazole group, and a thiazole group comprise a compound of the following Formula 3 or 4.

[Formula 3]

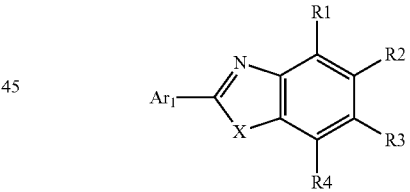

In Formula 3,

R1 and R4 may be the same as or different from each other, are each independently hydrogen; a $C_1$ to $C_{30}$ alkyl group which is unsubstituted or substituted with one or more groups selected from the group consisting of a halogen, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_3$ to $C_{30}$ cycloalkyl group which is unsubstituted or substituted with one or more groups selected from the group consisting of a halogen, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; a $C_5$ to $C_{30}$ aryl group which is unsubstituted or substituted with one or more groups selected from the group consisting of a halogen, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group; or a $C_2$ to $C_{30}$ heteroaryl group which is unsubstituted or substituted with one or more groups selected from the group consisting of a halogen, an amino group, a nitrile group, a nitro group, a $C_1$ to $C_{30}$ alkyl group, a $C_2$ to $C_{30}$ alkenyl group, a $C_1$ to $C_{30}$ alkoxy group, a $C_3$ to $C_{30}$ cycloalkyl group, a $C_3$ to $C_{30}$ heterocycloalkyl group, a $C_5$ to $C_{30}$ aryl group, and a $C_2$ to $C_{30}$ heteroaryl group, and may form an aliphatic, aromatic, aliphatic hetero, or aromatic hetero condensation ring or a spiro bond in conjunction with an adjacent group;

$Ar^1$ is hydrogen, a substituted or unsubstituted aromatic ring, or a substituted or unsubstituted aromatic heterocyclic ring;

X is O, S, or $NR^a$; and $R^a$ may be hydrogen, a C1 to C7 aliphatic hydrocarbon, an aromatic ring, or an aromatic heterocyclic ring.

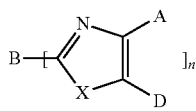

[Formula 4]

In Formula 4,

X is O, S, $NR^b$, or a $C_1$ to $C_7$ divalent hydrocarbon group;

A, D, and $R^b$ are each hydrogen, a nitrile group (—CN), a nitro group (—NO$_2$), a $C_1$ to $C_{24}$ alkyl, a substituted aromatic ring comprising a C5 to C20 aromatic ring or a hetero atom, a halogen, or an alkylene or an alkylene comprising a hetero atom which may form a fused ring in conjunction with an adjacent ring; A and D may be connected to each other to form an aromatic or hetero aromatic ring; B is a substituted or unsubstituted alkylene or arylene which conjugately or unconjugately connects multiple heterocyclic rings as a linkage unit when n is 2 or more, and a substituted or unsubstituted alkyl or aryl when n is 1; and n is an integer from 1 to 8.

Examples of the compound of Formula 3 comprise compounds disclosed in Korean Patent Application Laid-Open No. 2003-0067773, and examples of the compound of Formula 4 comprise compounds described in U.S. Pat. No. 5,645,948 and WO05/097756. All the contents of the documents are incorporated in the present specification.

Specifically, the compound of Formula 3 also comprises the following compound of Formula 5.

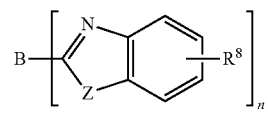

[Formula 5]

In Formula 5, $R^5$ to $R^7$ may be the same as or different from each other, and are each independently hydrogen, a $C_1$ to $C_{20}$ aliphatic hydrocarbon, an aromatic ring, an aromatic heterocyclic ring, or an aliphatic or aromatic condensation ring;

Ar is a direct bond, an aromatic ring, or an aromatic heterocyclic ring;

X is O, S, or $NR^a$; and $R^a$ is hydrogen, a $C_1$ to $C_7$ aliphatic hydrocarbon, an aromatic ring, or an aromatic heterocyclic ring; however, the case where $R^5$ and $R^6$ are simultaneously hydrogen is excluded.

Furthermore, the compound of Formula 4 also comprises the following compound of Formula 6.

[Formula 6]

In Formula 6,

Z is O, S, or $NR^b$; and $R^8$ and $R^b$ are hydrogen, a $C_1$ to $C_{24}$ alkyl, a substituted aromatic ring comprising a $C_5$ to $C_{20}$ aromatic ring or a hetero atom, a halogen, or an alkylene or an alkylene comprising a hetero atom which may form a fused ring in conjunction with a benzazole ring; B is an alkylene, an arylene, a substituted alkylene, or an unsubstituted arylene which conjugately or unconjugately connects multiple benzazoles as a linkage unit when n is 2 or more, and a substituted or unsubstituted alkyl or aryl when n is 1; and n is an integer from 1 to 8.

For example, imidazole compounds having the following structures may be used:

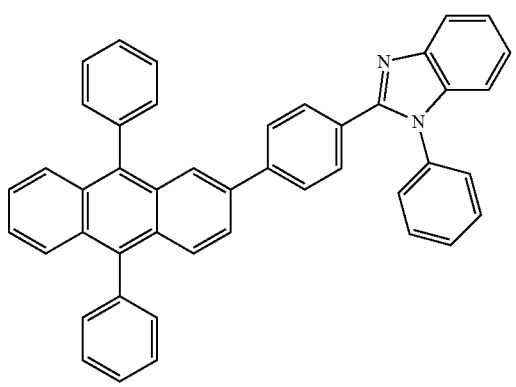

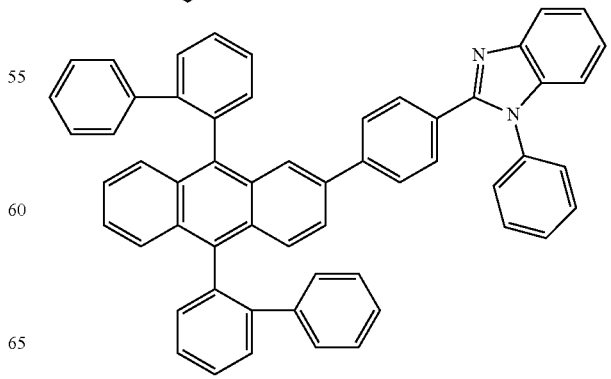

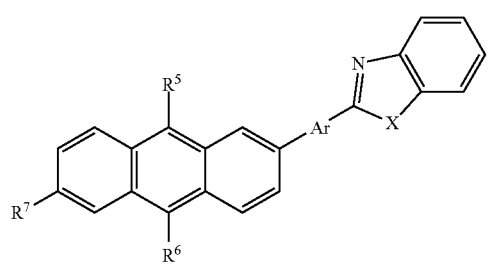

-continued
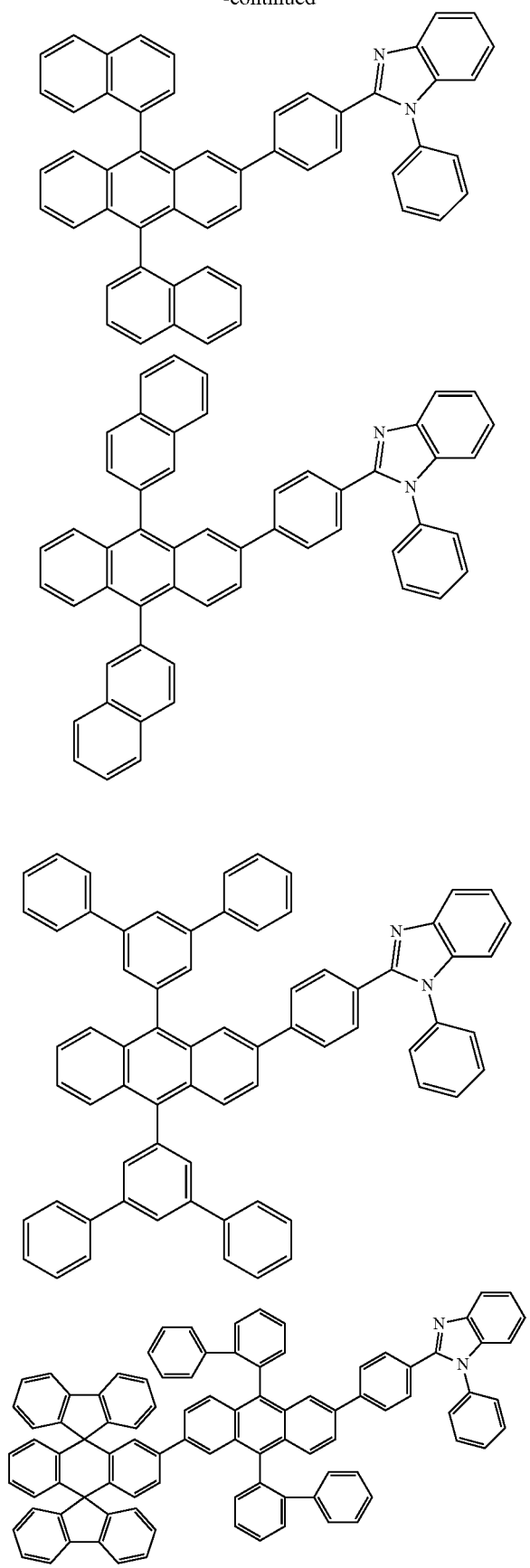
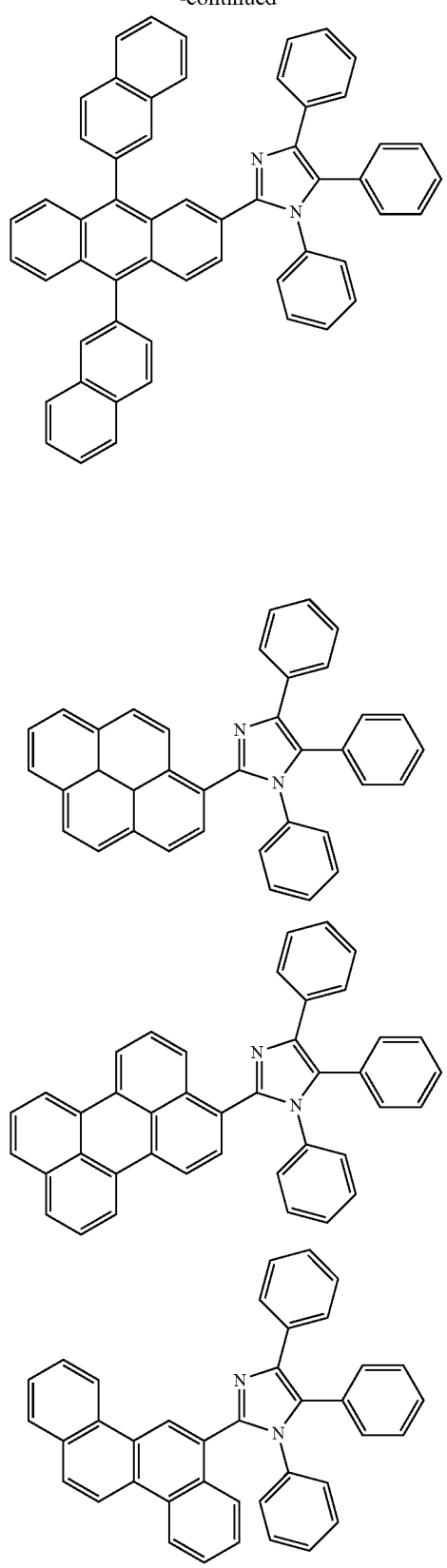
Examples of the quinoline group comprise the following compounds of Formulas 7 to 13.

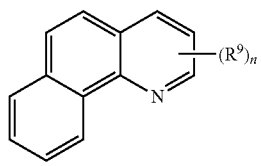

[Formula 7]

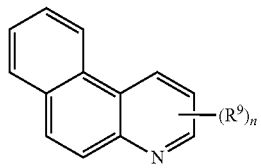

[Formula 8]

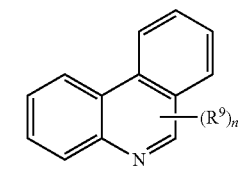

[Formula 9]

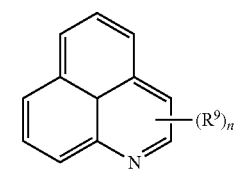

[Formula 10]

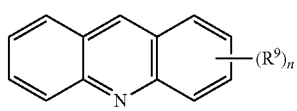

[Formula 11]

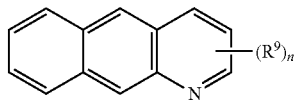

[Formula 12]

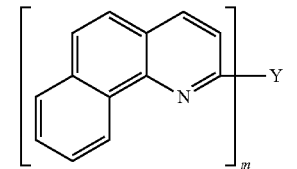

[Formula 13]

In Formulas 7 to 13, n is an integer from 0 to 9, and m is an integer of 2 or more, $R^9$ is selected from a ring structure with hydrogen, an alkyl group such a methyl group and an ethyl group, a cycloalkyl group such as cyclohexyl and norbornyl, an aralkyl group such as a benzyl group, an alkenyl group such as a vinyl group and an allyl group, a cycloalkenyl group such a cyclopentadienyl group and a cyclohexenyl group, an alkoxy group such as a methoxy group, an alkylthio group in which an oxygen atom with an ether bond of an alkoxy group is substituted with a sulfur atom, an aryl ether group such as a phenoxy group, an aryl thioether group in which an oxygen atom with an ether bond of an aryl ether group is substituted with a sulfur atom, an aryl group such as a phenyl group, a naphthyl group, and a biphenyl group, a heterocyclic group such as a furyl group, a thienyl group, an oxazolyl group, a pryridyl group, a quinolyl group, and a carbazolyl group, a halogen, a cyano group, an aldehyde group, a carbonyl group, a carboxyl group, an ester group, a carbamoyl group, an amino group, a nitro group, a silyl group such as a trimethylsilyl group, a siloxanyl group which is a group having silicon through an ether bond, and an adjacent substituent; and the substituents may be unsubstituted or substituted, and may be the same as or different from each other when n is 2 or more; and Y is a divalent or more group of the groups of $R^9$.

The compounds of Formulas 7 to 13 are described in Korean Patent Application Laid-Open No. 2007-0118711, and the content of the document is all incorporated in the present specification by reference.

Examples of the compound having a phenanthroline group comprise the following compounds of Formulas 14 to 24, but are not limited thereto.

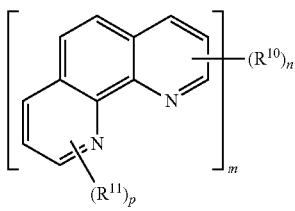

[Formula 14]

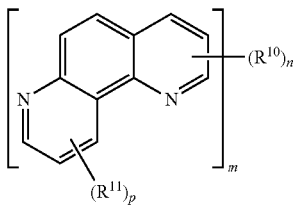

[Formula 15]

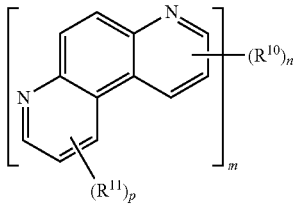

[Formula 16]

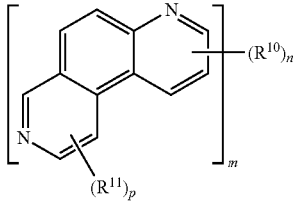

[Formula 17]

In Formulas 14 to 17, m is an integer of 1 or more, n and p are an integer, and n+p is 8 or less, when m is 1, $R^{10}$ and $R^{11}$ are selected from a ring structure with hydrogen, an alkyl group such a methyl group and an ethyl group, a cycloalkyl group such as cyclohexyl and norbornyl, an aralkyl group such as a benzyl group, an alkenyl group such as a vinyl group and an allyl group, a cycloalkenyl group such a cyclopentadienyl group and a cyclohexenyl group, an alkoxy group such as a methoxy group, an alkylthio group in which an oxygen atom with an ether bond of an alkoxy group is substituted with a sulfur atom, an aryl ether group such as a phenoxy group, an aryl thioether group in which an oxygen atom with an ether bond of an aryl ether group is substituted with a sulfur atom, an aryl group such as a phenyl group, a naphthyl group, and a biphenyl group, a heterocyclic group such as a furyl group, a thienyl group, an oxazolyl group, a pryridyl group, a quinolyl group, and a carbazolyl group, a halogen, a cyano group, an aldehyde group, a carbonyl group, a carboxyl group, an ester group, a carbamoyl group, an amino group, a nitro group, a silyl group such as a trimethylsilyl group, a siloxanyl group which is a group having silicon through an ether bond, and an adjacent substituent;

when m is 2 or more, $R^{10}$ is a direct bond or a divalent or more group of the above-described groups, and $R^{11}$ is the same as the case where m is 1, the substituents may be unsubstituted or substituted, and when n or p is 2 or more, the substituents may be the same as or different from each other.

The compounds of Formulas 14 to 17 are described in Korean Patent Application Laid-Open Nos. 2007-0052764 and 2007-0118711, and the contents of the documents are all incorporated in the present specification by reference.

[Formula 18]

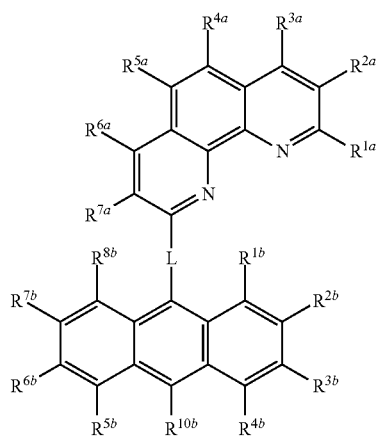

[Formula 19]

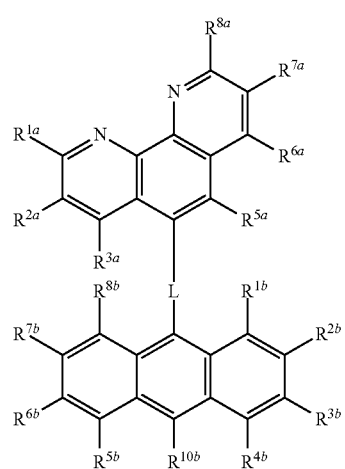

[Formula 20]

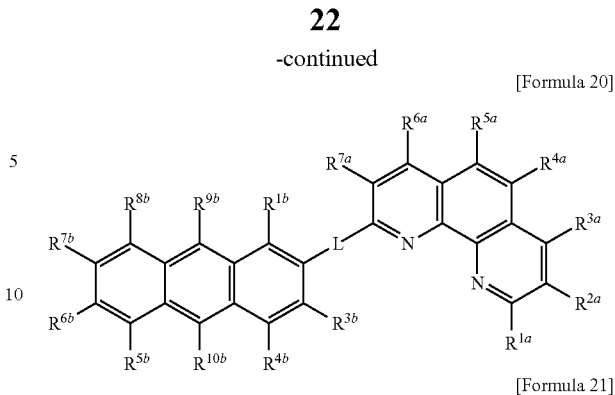

[Formula 21]

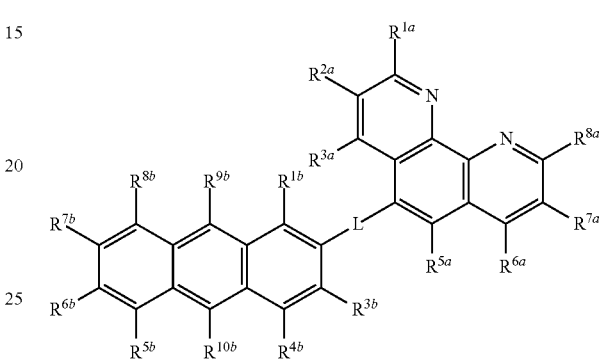

In Formulas 18 to 21, $R^{1a}$ to $R^{8a}$ and $R^{1b}$ to $R^{10b}$ are each a hydrogen atom, a substituted or unsubstituted aryl group having from 5 to 60 nucleus atoms, a substituted or unsubstituted pyridyl group, a substituted or unsubstituted quinolyl group, a substituted or unsubstituted alkyl group having from 1 to 50, a substituted or unsubstituted cycloalkyl group having from 3 to 50 carbon atoms, a substituted or unsubstituted aralkyl group having from 6 to 50 nucleus atoms, a substituted or unsubstituted alkoxy group having from 1 to 50 carbon atoms, a substituted or unsubstituted aryloxy group having from 5 to 50 nucleus atoms, a substituted or unsubstituted arylthio group having from 5 to 50 nucleus atoms, a substituted or unsubstituted alkoxycarbonyl group having from 1 to 50 carbon atoms, an amino group substituted with a substituted or unsubstituted aryl group having from 5 to 50 nucleus atoms, a halogen atom, a cyano group, a nitro group, a hydroxyl group, or a carboxyl group, and may be bonded to each other to from an aromatic ring, and L is a substituted or unsubstituted arylene group having from 6 to 60 carbon atoms, a substituted or unsubstituted pyridinylene group, a substituted or unsubstituted quinolinylene group, or a substituted or unsubstituted fluorenylene group. The compounds of Formulas 18 to 21 are described in Japanese Patent Application Laid-Open No. 2007-39405, and the content of the document is all incorporated in the present specification by reference.

[Formula 22]

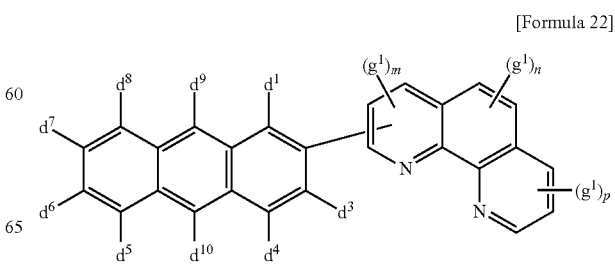

[Formula 23]

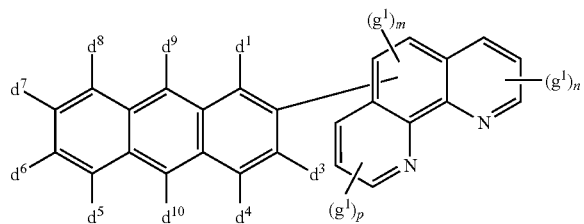

In Formulas 22 and 23, $d^1$, $d^3$ to $d^{10}$, and $g^1$ are each hydrogen, or an aromatic or aliphatic hydrocarbon group, m and n are an integer from 0 to 2, and p is an integer from 0 to 3. The compounds of Formulas 22 and 23 are described in US Patent Application Publication No. 2007/0122656, and the content of the document is all incorporated in the present specification by reference.

[Formula 24]

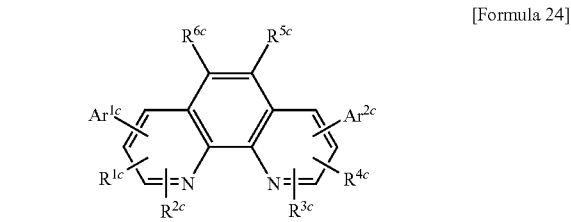

In Formula 24, $R^{1c}$ to $R^{6c}$ are each a hydrogen atom, a substituted or unsubstituted alkyl group, a substituted or unsubstituted aralkyl group, a substituted or unsubstituted aryl group, a substituted or unsubstituted heterocyclic group, or a halogen atom, and $Ar^{1c}$ and $Ar^{2c}$ are each selected from the following structural formulas.

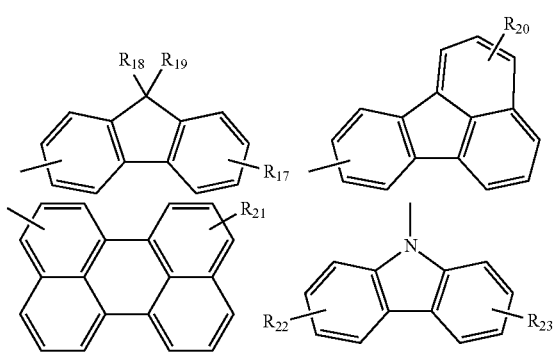

In the structural formulas, $R_{17}$ to $R_{23}$ are each a hydrogen atom, a substituted or unsubstituted alkyl group, a substituted or unsubstituted aralkyl group, a substituted or unsubstituted aryl group, a substituted or unsubstituted heterocyclic group, or a halogen atom. The compound of Formula 24 is described in Japanese Patent Application Laid-Open No. 2004-107263, and the content of the document is all incorporated in the present specification by reference.

Cathode

In the present specification, a cathode material may be selected from materials having various work functions. It is preferred that the cathode material is usually a material having a small work function so as to facilitate electron injection. However, in the present specification, a material having a large work function may also be applied. Specifically, in the present specification, it is possible to use, as the cathode material, a material having a work function which is equal to or larger than the HOMO of the above-described p-type organic material layer. For example, in the present specification, a material having a work function from 2 eV to 5 eV may be used as the cathode material. The cathode comprises a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al, and the like.

The cathode may be formed of a material which is the same as the anode. Alternatively, the cathode or the anode may comprise a transparent material.

In the present invention, the anode may be opaque, and the first cathode and the second cathode may be transparent. At this time, the anode comprises a metal, and the anode may have a thickness from 50 nm to 200 nm. In addition, the first cathode and the second cathode each independently comprise a metal or a metal oxide, and may each independently have a thickness from 5 nm to 200 nm.

Furthermore, in the present invention, the anode, the first cathode, and the second cathode may be all opaque. Here, the anode, the first cathode, and the second cathode each independently comprise a metal or a metal oxide, and may each independently have a thickness from 5 nm to 200 nm.

In the present invention, the first light emitting unit may further comprise a third light emitting layer. Here, the organic material layer represented by Formula 1 may be further comprised between the first light emitting layer and the third light emitting layer.

Further, in the present invention, the second light emitting unit may further comprise a fourth light emitting layer. Here, the organic material layer represented by Formula 1 may be further comprised between the second light emitting layer and the fourth light emitting layer.

As the organic light emitting device according to an exemplary embodiment of the present invention, an organic light emitting device further comprising the third light emitting layer and the fourth light emitting layer is illustrated in the following FIG. 3.

In the present invention, the first light emitting layer, the second light emitting layer, the third light emitting layer, and the fourth light emitting layer may emit light having the same or different color.

In particular, it is preferred that the organic light emitting device according to the present invention has a structure in which the first light emitting unit and the second light emitting unit are symmetric with each other with respect to the anode.

Meanwhile, in the organic light emitting device, it is possible to use a method of controlling a cavity of the device according to a light emitting color as one of the methods of increasing light emitting efficiency. The light emitting efficiency may be further increased by controlling the cavity of the device so as to be suitable for a wavelength of the light emitting color. Here, the cavity of the device means a length within which light may be resonated in the device.

As described above, when the organic light emitting device in the related art as in FIG. 1 comprises two light emitting layers, the cavity lengths thereof are different from each other, and therefore there is a problem in that it is difficult to implement a desired color.

However, the present invention has characteristics that the cavity lengths may be controlled to be the same as each other as in the structures of FIGS. 1 and 2 by comprising the anode as an intermediate electrode and connecting two light emitting units in parallel, and accordingly, a desired color may be implemented.

[Best Mode]

Hereinafter, specific examples of the above-described exemplary embodiments will be described. However, the following examples are illustrative only, and are not intended to limit the range of the exemplary embodiments.

EXAMPLES

Example 1

An IZO was formed as a first cathode to have a thickness of 1,500 Å on a substrate. An electron transporting layer having a thickness of 50 Å was formed thereon by doping an electron transporting material of the following formula with Ca in an amount of 10% by weight, and subsequently, an organic material layer having a thickness of 250 Å was formed using the electron transporting material of the following formula.

A hole blocking layer having a thickness of 75 Å was formed thereon using a BCP of the following formula. Subsequently, a light emitting layer having a thickness of 300 Å was formed by doping a CBP of the following formula with an Ir(ppy)$_3$ of the following formula in an amount of 20% by weight.

A p-type hole transporting layer having a thickness of 300 Å was formed thereon by vacuum depositing an NPB of the following formula, and an n-type hole injection layer having a thickness of 300 Å was formed thereon by thermally vacuum depositing an HAT of the following formula, thereby completing a first light emitting part.

Subsequently, Al was formed as a common anode to have a thickness of 700 Å.

Thereafter, the HAT as an n-type hole injection layer was deposited to have a thickness of 300 Å, and the NPB as a p-type hole transporting layer was formed to have a thickness of 300 Å.

A light emitting layer having a thickness of 300 Å was formed thereon by doping the CBP of the following Formula with the Ir(ppy)$_3$ of the following formula in an amount of 10% by weight.

Thereafter, the BCP as a hole blocking layer was formed to have a thickness of 50 Å, and an organic material layer having a thickness of 250 Å was formed using the electron transporting material of the following formula. Thereafter, an electron injection layer was formed by doping the electron transporting material of the following formula with Ca in an amount of 10% by weight, thereby completing a second light emitting part.

Finally, a second cathode layer was formed by forming Ag having a thickness of 100 Å, thereby manufacturing a dual emission type organic light emitting device.

For the quantum efficiency (@10 mA/cm$^2$) of the device manufactured, the efficiency of light emitted on the electrode surface of the first cathode was 15% and the efficiency of light emitted on the electrode surface of the second cathode was 12%, and a high light efficiency may be obtained on both surfaces thereof. The difference between efficiencies of light emitted on both surfaces was at about 1.25:1 level. At that time, the device driving voltage was measured as 8.5 V.

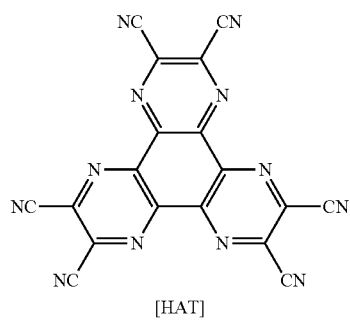

[HAT]

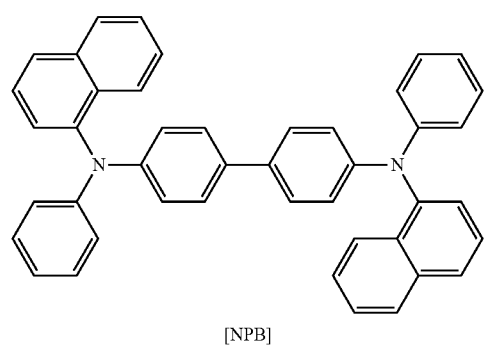

[NPB]

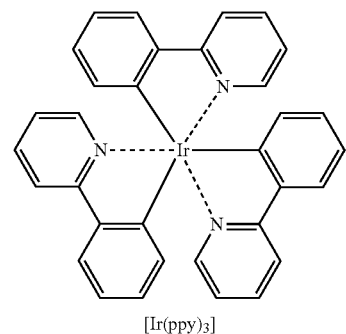

[Ir(ppy)$_3$]

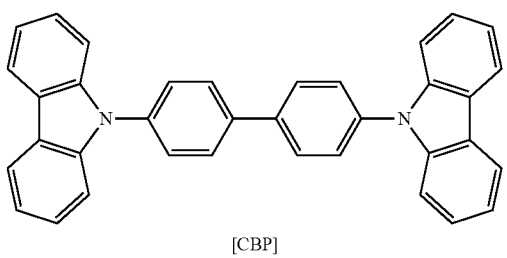

[CBP]

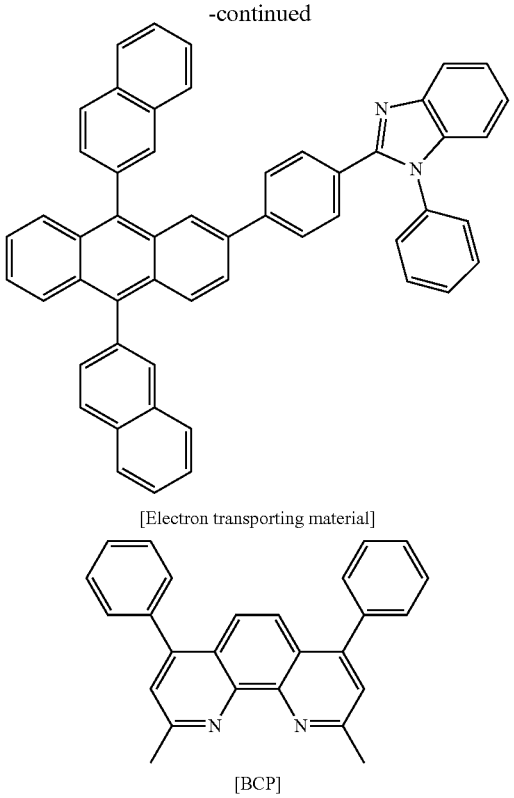

[Electron transporting material]

[BCP]

Example 2

A transparent dual emission type organic light emitting device was manufactured was manufactured in the same manner as in Example 1, except that the anode as the intermediate common electrode was composed of Ag having a thickness of 100 Å as a transparent electrode. For the quantum efficiency (@10 mA/cm$^2$) of the device manufactured, the efficiency of light emitted on the electrode surface of the first cathode was measured as 9% and the efficiency of light emitted on the electrode surface of the second cathode was measured as 7%, and the light efficiency of both surfaces thereof was at about 1.3:1 level. At that time, the device driving voltage was measured as 8.5 V.

Comparative Example 1

A device was manufactured in the same manner as in Example 1, except that the HAT as a layer which was in contact with the common anode as an intermediate electrode in top and bottom directions was not formed. In the device manufactured, holes was not smoothly injected from Al as the anode to NPB as the hole transfer layer such that a normal light emitting action was not performed.

Comparative Example 2

An IZO was formed as an anode to have a thickness of 1,500 Å on a substrate.
Thereafter, the HAT as an n-type hole injection layer was deposited to have a thickness of 300 Å, and the NPB as a p-type hole transporting layer was formed to have a thickness of 300 Å.

A light emitting layer having a thickness of 300 Å was formed thereon by doping the CBP of the above Formula with Ir(ppy)$_3$ of the above formula in an amount of 10% by weight.

Thereafter, the BCP as a hole blocking layer was formed to have a thickness of 50 Å, and an organic material layer having a thickness of 250 Å was formed using the electron transporting material of the above formula. Thereafter, an electron injection layer was formed by doping the electron transporting material of the above formula with Ca in an amount of 10% by weight, thereby completing a second light emitting part.

Finally, a cathode layer was formed by forming Ag having a thickness of 100 Å, thereby manufacturing a transparent dual emission type organic light emitting device. For the quantum efficiency (@ 10 mA/cm$^2$) of the device manufactured, the efficiency of light emitted on the electrode surface of the first cathode was measured as 9%, and the efficiency of light emitted on the electrode surface of the second cathode was measured as 3%, and the light efficiency ratio of both surfaces thereof was about 3:1.

As seen in the result, the organic light emitting device according to the present invention may be applied to a dual emission type organic light emitting device by symmetrically connecting two light emitting units to an anode which is a common electrode on and under the anode. In addition, the organic light emitting device according to the present invention may use electrode materials having various work functions by comprising organic material layers comprising the compound represented by Formula 1.

The invention claimed is:
1. An organic light emitting device comprising:
a first cathode;
a second cathode; and
an anode provided between the first cathode and the second cathode,
wherein a first light emitting unit is provided between the first cathode and the anode, a second light emitting unit is provided between the second cathode and the anode, and the first light emitting unit and the second emitting unit are connected in parallel with each other,
the first light emitting unit comprises a first light emitting layer, and an organic material layer comprising a compound represented by the following Formula 1 is provided between the first light emitting layer and the anode, and
the second light emitting unit comprises a second light emitting layer, and an organic material layer comprising the compound represented by the following Formula 1 is provided between the second light emitting layer and the anode,
wherein the anode is opaque, and the first cathode and the second cathode are transparent,

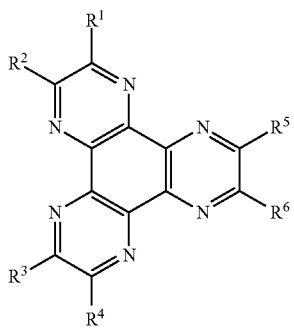

[Formula 1]

in Formula 1,

R$^1$ to R$^6$ are the same as or different from each other, and each independently hydrogen, a halogen atom, nitrile (—CN), nitro (—NO2), sulfonyl (—SO2R), sulfoxide (—SOR), sulfonamide (—SO2NR), sulfonate (—SO3R), trifluoromethyl (—CF3), ester (—COOR), amide (—CONHR or —CONRR'), a substituted or unsubstituted straight or branched C1 to C12 alkoxy, a substituted or unsubstituted straight or branched C1 to C12 alkyl, a substituted or unsubstituted straight or branched C2 to C12 alkenyl, a substituted or unsubstituted aromatic or non-aromatic heterocyclic ring, a substituted or unsubstituted aryl, a substituted or unsubstituted mono- or di-aryl amine, or a substituted or unsubstituted aralkyl amine, wherein R and R' are each independently a substituted or unsubstituted C1 to C60 alkyl, a substituted or unsubstituted aryl, or a substituted or unsubstituted 5- to 7-membered heterocyclic ring.

2. The organic light emitting device of claim 1, wherein at least one of the organic material layers comprising the compound represented by Formula 1 is an organic material layer which is in contact with the anode.

3. The organic light emitting device of claim 1, wherein the organic light emitting device is a dual emission type.

4. The organic light emitting device of claim 1, wherein the anode comprises a metal, and has a thickness from 50 nm to 200 nm.

5. The organic light emitting device of claim 1, wherein the first cathode and the second cathode each independently comprise a metal or a metal oxide, and each independently have a thickness from 5 nm to 200 nm.

6. The organic light emitting device of claim 1, wherein the first light emitting unit further comprises a third light emitting layer.

7. The organic light emitting device of claim 6, further comprising:
the organic material layer represented by Formula 1 between the first light emitting layer and the third light emitting layer.

8. The organic light emitting device of claim 1, wherein the second light emitting unit further comprises a fourth light emitting layer.

9. The organic light emitting device of claim 8, further comprising:
the organic material layer represented by Formula 1 between the second light emitting layer and the fourth light emitting layer.

10. The organic light emitting device of claim 1, wherein the first light emitting layer and the second light emitting emit light having the same or different color.

11. The organic light emitting device of claim 1, wherein the organic light emitting device has a structure in which the first light emitting unit and the second light emitting unit are symmetric with each other with respect to the anode.

* * * * *